US008163725B1

(12) United States Patent
Buge et al.

(10) Patent No.: US 8,163,725 B1
(45) Date of Patent: Apr. 24, 2012

(54) GEL COMPOSITIONS AND METHODS OF USE

(75) Inventors: Jean-Christophe Buge, Nice (FR); Karine Nadau-Fourcade, Villeneuve-Loubet (FR); Cyril Meunier, Mougins (FR)

(73) Assignee: Galderma R&D SNC, Biot (FR)

( * ) Notice: Subject to any disclaimer, the term of this patent is extended or adjusted under 35 U.S.C. 154(b) by 0 days.

(21) Appl. No.: 13/240,562

(22) Filed: Sep. 22, 2011

Related U.S. Application Data

(62) Division of application No. 13/158,987, filed on Jun. 13, 2011, now Pat. No. 8,053,427.

(60) Provisional application No. 61/405,388, filed on Oct. 21, 2010.

(51) Int. Cl.
| | |
|---|---|
| *A61K 31/45* | (2006.01) |
| *A61K 31/535* | (2006.01) |
| *A61K 31/415* | (2006.01) |
| *A61K 31/135* | (2006.01) |
| *A61K 51/00* | (2006.01) |
| *A61K 8/00* | (2006.01) |
| *A61K 8/18* | (2006.01) |
| *A01N 43/58* | (2006.01) |
| *A01N 43/60* | (2006.01) |
| *A01N 43/50* | (2006.01) |
| *A01N 33/02* | (2006.01) |
| *A61M 36/14* | (2006.01) |
| *A61Q 17/04* | (2006.01) |

(52) U.S. Cl. ............. 514/181; 514/401; 514/234.8; 514/249; 514/400; 514/649; 514/651; 514/653; 424/1.25; 424/59; 424/78.05; 424/400; 424/401; 424/449; 424/455

(58) Field of Classification Search .................. None
See application file for complete search history.

(56) References Cited

U.S. PATENT DOCUMENTS

| | | | |
|---|---|---|---|
| 3,278,447 A | 10/1966 | McNicholas | |
| 3,560,501 A | 2/1971 | Walker | |
| 3,594,380 A | 7/1971 | Sulkowski | |
| 3,723,432 A | 3/1973 | Ott | |
| 3,736,297 A | 5/1973 | Bracke | |
| 3,740,442 A | 6/1973 | Ott | |
| 3,890,319 A | 6/1975 | Danielewicz et al. | |
| 4,029,792 A | 6/1977 | Danielewicz et al. | |
| 4,164,570 A | 8/1979 | Clough et al. | |
| 4,201,211 A | 5/1980 | Chandrasekaran et al. | |
| 4,256,763 A | 3/1981 | McHugh | |
| 4,285,967 A | 8/1981 | Gubernick et al. | |
| 5,021,416 A | 6/1991 | Gluchowski | |
| 5,077,292 A | 12/1991 | Gluchowski | |
| 5,112,822 A | 5/1992 | Gluchowski | |
| 5,130,441 A | 7/1992 | Gluchowski | |
| 5,198,442 A | 3/1993 | Gluchowski | |
| 5,204,347 A | 4/1993 | Gluchowski | |
| 5,237,072 A | 8/1993 | Gluchowski | |
| 5,300,504 A | 4/1994 | Gluchowski | |
| 5,326,763 A | 7/1994 | Gluchowski et al. | |
| 5,373,010 A | 12/1994 | Gluchowski et al. | |
| 5,418,234 A | 5/1995 | Gluchowski et al. | |
| 5,424,078 A | 6/1995 | Dziabo et al. | |
| 5,442,053 A | 8/1995 | della Valle et al. | |
| 5,552,403 A | 9/1996 | Burke et al. | |
| 5,561,132 A | 10/1996 | Burke et al. | |
| 5,587,376 A | 12/1996 | Burke et al. | |
| 5,693,646 A | 12/1997 | Jones et al. | |
| 5,696,127 A | 12/1997 | Jones et al. | |
| 5,703,077 A | 12/1997 | Burke et al. | |
| 5,714,486 A | 2/1998 | Burke et al. | |
| 5,720,962 A | 2/1998 | Ivy et al. | |
| 5,721,237 A | 2/1998 | Myers et al. | |
| 5,736,165 A | 4/1998 | Ripley et al. | |
| 5,753,637 A | 5/1998 | Fried | |
| 5,756,503 A | 5/1998 | Burke et al. | |
| 5,773,440 A | 6/1998 | Burke et al. | |
| 5,916,574 A | 6/1999 | Fried et al. | |
| 6,007,846 A | 12/1999 | Klar | |
| 6,117,871 A | 9/2000 | Maurer et al. | |
| 6,117,877 A | 9/2000 | Fogel | |
| 6,194,415 B1 | 2/2001 | Wheeler et al. | |
| 6,248,741 B1 | 6/2001 | Wheeler et al. | |
| 6,284,765 B1 | 9/2001 | Caffrey | |
| 6,294,553 B1 | 9/2001 | Gil et al. | |
| 6,294,563 B1 | 9/2001 | Garst | |
| 6,323,204 B1 | 11/2001 | Burke et al. | |
| 6,387,383 B1 | 5/2002 | Dow et al. | |
| 6,432,934 B1 | 8/2002 | Gilbard | |
| 6,441,047 B2 | 8/2002 | DeSantis, Jr. | |

(Continued)

FOREIGN PATENT DOCUMENTS

EP 1090630 A1 4/2001

(Continued)

OTHER PUBLICATIONS

Arndt et al, "Manual of Dermatologic Therapeutics", 7th Ed., pp. 176-177 (2007).
Berge et al, "Pharmaceutical Salts" Journal of Pharmaceutical Sciences, vol. 66, No. 1, pp. 1-19 (1977).
Bockman et al, "Binding and Functional Characterization of Alpha-2 Andrenergic Receptor Subtypes on Pig Vascular Endothelium", J. Pharmacol Exp. Therapeutics, vol. 267, pp. 1126-1133 (1993).
Burke et al, "Preclinical Evaluation of Brimonidine", Survey of Ophthalmology, vol. 41, pp. S9-S18 (1996).
Chein et al, "Corneal and conjunctival/scleral penetration of p-aminoclonidine, AGN 190342 and clonidine in rabbit eyes", Current Eye Research, vol. 9, No. 11 pp. 1051-1059 (1990).
Chotani et al, "Silent asc-adrenergic receptors enable cold-induced vasoconstriction in cutaneous arteries", Am. J. Physiol. Heart Circ. Physiol., vol. 278, pp. H1075-H1083 (2000).
Cunliffe et al, Br. Med. J. 105 (1977).

(Continued)

*Primary Examiner* — Jeffrey S. Lundgren
*Assistant Examiner* — William Lee
(74) *Attorney, Agent, or Firm* — Panitch Schwarze Belisario & Nadel LLP

(57) ABSTRACT

Improved topical gel compositions for the treatment of skin disorders are described. The gel compositions contain carbomer and methylparaben, and are substantially free of methylparaben crystalline particles after an extended period of storage.

18 Claims, No Drawings

U.S. PATENT DOCUMENTS

| | | | |
|---|---|---|---|
| 6,444,681 | B1 | 9/2002 | Flavahan et al. |
| 6,465,464 | B2 | 10/2002 | Wheeler et al. |
| 6,468,989 | B1 | 10/2002 | Chang et al. |
| 6,517,847 | B2 | 2/2003 | Dow et al. |
| 6,534,048 | B1 | 3/2003 | Borgman |
| 7,001,615 | B1 | 2/2006 | Singh et al. |
| 7,014,858 | B2 | 3/2006 | Ashley |
| 7,439,241 | B2 | 10/2008 | DeJovin et al. |
| 7,709,533 | B2 | 5/2010 | Wang et al. |
| 7,812,049 | B2 | 10/2010 | Shanler et al. |
| 7,838,563 | B2 | 11/2010 | DeJovin et al. |
| 8,053,427 | B1 * | 11/2011 | Buge et al. ............... 514/401 |
| 2002/0197300 | A1 | 12/2002 | Schultz et al. |
| 2003/0017199 | A1 | 1/2003 | Woodward et al. |
| 2003/0068343 | A1 | 4/2003 | Muizzuddin et al. |
| 2003/0077301 | A1 | 4/2003 | Maibach et al. |
| 2003/0087962 | A1 | 5/2003 | Demopulos et al. |
| 2003/0229088 | A1 | 12/2003 | Gil et al. |
| 2004/0092482 | A1 | 5/2004 | Gupta |
| 2004/0156873 | A1 | 8/2004 | Gupta |
| 2004/0220259 | A1 | 11/2004 | Yu et al. |
| 2004/0242588 | A1 | 12/2004 | Dejovin et al. |
| 2004/0254252 | A1 | 12/2004 | Engles et al. |
| 2004/0266776 | A1 | 12/2004 | Gil et al. |
| 2005/0020600 | A1 | 1/2005 | Scherer |
| 2005/0059664 | A1 | 3/2005 | Gil et al. |
| 2005/0059744 | A1 | 3/2005 | Donello et al. |
| 2005/0196418 | A1 | 9/2005 | Yu et al. |
| 2005/0276830 | A1 | 12/2005 | DeJovin et al. |
| 2006/0057081 | A1 | 3/2006 | Boxrud |
| 2006/0171974 | A1 | 8/2006 | DeJovin et al. |
| 2006/0264515 | A1 | 11/2006 | Dejovin et al. |
| 2007/0003622 | A1 | 1/2007 | Srinivasan et al. |
| 2007/0082070 | A1 | 4/2007 | Stookey et al. |
| 2007/0207222 | A1 | 9/2007 | Yu et al. |
| 2007/0258935 | A1 | 11/2007 | McEntire et al. |
| 2008/0181867 | A1 | 7/2008 | Lambert et al. |
| 2008/0293728 | A1 | 11/2008 | McIntire et al. |
| 2009/0060852 | A1 | 3/2009 | DeJovin et al. |
| 2009/0061020 | A1 | 3/2009 | Theobald et al. |
| 2009/0130027 | A1 | 5/2009 | Shanler et al. |
| 2010/0021402 | A1 | 1/2010 | DeJovin et al. |
| 2010/0028267 | A1 | 2/2010 | Horn |
| 2010/0055153 | A1 | 3/2010 | Majmudar |
| 2010/0130502 | A1 | 5/2010 | DeJovin et al. |
| 2010/0227867 | A1 | 9/2010 | DeJovin et al. |
| 2011/0118267 | A1 | 5/2011 | DeJovin |

FOREIGN PATENT DOCUMENTS

| | | |
|---|---|---|
| EP | 2090307 A1 | 8/2009 |
| EP | 2213335 A2 | 8/2010 |
| GB | 1381979 A | 1/1975 |
| WO | 9100088 A1 | 1/1991 |
| WO | 9613267 A2 | 5/1996 |
| WO | 9625163 A1 | 8/1996 |
| WO | 9836730 A2 | 8/1998 |
| WO | 0076502 A1 | 12/2000 |
| WO | 2004105703 A2 | 12/2004 |
| WO | 2005002580 A1 | 1/2005 |
| WO | 2005010025 A2 | 2/2005 |
| WO | 2009082452 A1 | 7/2009 |
| WO | 2009158646 A1 | 12/2009 |
| WO | 2010136585 A2 | 12/2010 |
| WO | 2011053487 A1 | 5/2011 |

OTHER PUBLICATIONS

Freedman et al, "Estrogen raises the sweating threshold in postmenopausal women with hot flashes", Fertility and Sterility, vol. 77, No. 3, pp. 487-490 (2002).

Fuchs et al, "Heat, but not Mechanical Hyperalgesia, following Andrenergic Injections in Normal Human Skin", Pain, vol. 90, Nos. 1-2, pp. 15-23 (2001).

Gennaro, "Remington: The Science and Practice of Pharmacy", 19th Ed., pp. 866-885, 1517-1518, 1577-1597, 1672-1673 (1995).

Guarrera et al, "Flushing in Rosacea: A Possible Mechanism", Arch. Dermatol. Res., vol. 272, pp. 311-316 (1982).

Int'l Search Report issued on Mar. 29, 2011 in Int'l Application No. PCT/US2010/057184; Written Opinion.

Jeyara et al, "Cooling Evokes Redistribution of a2C-Andrenoceptors from Golgi to Plasma Membrane in Transfected Human Embryonic Kidney 293 Cells", Molecular Pharmacology, vol. 60, No. 6, pp. 1195-1200 (2001).

Lindgren et al, "Effects of Some Antihypertensive Drugs on Cutaneous Blood Flow and Inflammatory Skin Responses Following Allergen Challenge in Guinea Pigs", Pharmacology and Toxicology, vol. 60, pp. 364-367 (1987).

Material Safety Data Sheet, pp. 1-2 (1997).

McGhie, "Brimonidine: An alpha-2 adrenergic agonist for glaucoma", Journal of the Pharmacy Society of Wisconsin, May/Jun. 2001, pp. 32-36.

Morrison et al, "Andrenergic Modulation of a Spinal Sympathetic Reflex in the Rat", J. Pharmacol. Experim. Therap., vol. 273, No. 1, pp. 380-385 (1995).

Nakamura et al, "Peripheral analgesic action of clonidine: mediation by release of endogenous enkephlin-like substances", European Journal of Pharmacology, vol. 146, pp. 223-228 (1988).

Nielsen et al, "Postjunctional a2-adrenoceptors mediate vasoconstriction in human subcutaneous resistance vessels", Br. J. Pharmacol., vol. 97, pp. 829-834 (1989).

Ramey et al, "Rhinitis Medicamentosa", J Investig Allergol Clin Immunol, vol. 16, No. 3, pp. 148-155 (2006).

Rebora, "The Management of Rosacea", Am. J. Clin. Dermatol., vol. 3, No. 7, pp. 489-496 (2002).

Sakakibara et al, "Treatment of Primary Erythromelalgia with Cyproheptadine", Journal of the Autonomic Nervous System, vol. 58, Nos. 1-2, pp. 121-122 (1996).

Scruggs, "The Teardrop Sign: a Rare Dermatological Reaction to Brimonidine", Br. J. Opthalmol., vol. 84, pp. 671-672 (2000).

Shanler et al, "Arch Dermatol", vol. 143, No. 11, pp. 1369-1371 (2007).

Waldron et al, "Relative Contribution of Different Vascular Beds to the Pressor Effects of a-Adrenoceptor Agonists and Vasopressin in Pithed Rats: Radioactive Microsphere Determination", J. Auton. Pharmac., vol. 5, pp. 333-338 (1985).

Walters, "Development and Use of Brimonidine in Treating Acute and Chronic Elevations of Intraocular Pressure: A Review of Safety, Efficacy, Dose Response, and Dosing Studies", Survey of Ophthalmology, vol. 41, pp. S19-S26 (1996).

Webster, "Rosacea and related disorders", Dermatology, vol. 1, Chapter 39, pp. 545-552 (2003).

Wilkin et al, J. Am. Acad. Dermatol., vol. 46, pp. 584-587 (2002).

Wilkin, "Effect of Subdepressor Clonidine on Flushing Reactions in Rosacea", Arch. Dermatol., vol. 119, pp. 211-214 (1983).

Wilkin, "Why is flushing limited to a mostly facial cutaneous distribution?", J. Am. Acad. Dermatol., vol. 19, pp. 309-313 (1988).

Wymenga et al, "Management of Hot Flushes in Breast Cancer Patients", Acta Ocologica, vol. 41, No. 3, pp. 269-275 (2002).

Yaksh et al, "Reversal of Nerve Ligation-Induced Allodynia by Spinal Alpha-2 Andrenoceptor Agonists", J. Pharmacol. Experim. Therap., vol. 272, No. 1, pp. 207-214 (1995).

Search Report issued Jun. 1, 2011 in FR Application No. 1058612; Written Opinion.

Giordano et al, "Physical Properties of Parabens and Their Mixtures: Solubility in Water, Thermal Behavior, and Crystal Structures," Journal of Pharmaceutical Sciences, vol. 88, No. 11, pp. 1210-1216 (1999).

Perlovich et al, "Thermodynamics of solubility, sublimation and solvation processes of parabens," European Journal of Pharmaceutical Sciences, vol. 24, pp. 25-33 (2005).

Office Action issued Jul. 21, 2011 in U.S. Appl. No. 13/158,987.

* cited by examiner

GEL COMPOSITIONS AND METHODS OF USE

CROSS-REFERENCE TO RELATED APPLICATIONS

This application is a divisional application of U.S. patent application Ser. No. 13/158,987, filed on Jun. 13, 2011, which is entitled to priority pursuant to 35 U.S.C. §119(e) to U.S. Provisional Patent Application No. 61/405,388, filed Oct. 21, 2010, the disclosures of which are hereby incorporated by reference herein in its entirety.

BACKGROUND OF THE INVENTION

Parabens are esters of para-hydroxybenzoic acid. They are used primarily for their bactericidal and fungicidal properties. Examples of parabens include methylparaben, ethylparaben, propylparaben, butylparaben, isobutylparaben, isopropylparaben, benzylparaben and their salts. Because of their low costs, long history of safe use and the inefficacy of natural alternatives, parabens are widely used as preservatives in the cosmetic and pharmaceutical industries. See Darbre et al., 24 J. Appl. Toxicol. 5-13 (2004) and references therein.

Carbomer is a generic name of Carbopol®, a trademarked product from Lubrizol. Carbomer and Carbopol® are used interchangeably in the present application, referring to a synthetic polymer of acrylic acid cross-linked with polyalkenyl ethers or divinyl glycol. It can be a homopolymer of acrylic acid, cross-linked with an allyl ether pentaerythritol, allyl ether of sucrose, or allyl ether of propylene. Carbomers have been used as vehicles for drug delivery. They have a long history of safe and effective use in topical gels, creams, lotions, and ointments, as supported by extensive toxicology studies. They have been shown to have extremely low irritancy properties and are non-sensitizing with repeat usage. Carbomers or carbomer copolymers have been used in topical formulations, e.g., for thickening, emulsifying or suspending.

Brimonidine is a selective alpha-2-adrenergic agonist. It has been used as either monotherapy or as adjunctive therapy to lower intraocular pressure (IOP) in the treatment of glaucoma and ocular hypertension (OHT) since its approval in 1996. Brimonidine has also been found to be useful in treating various skin disorders, such as rosacea, erythema caused by rosacea, see, e.g., U.S. Ser. No. 10/853,585 to DeJovin et al.; U.S. Ser. No. 10/626,037 to Scherer; U.S. Ser. No. 12/193,098 to Theobald et al.; telangiectasias, see, e.g., U.S. Patent Application Publication No. 2006/0264515. Topical gel compositions comprising brimonidine, carbomer and paraben(s) for the treatment of skin disorders have been described, see for example, U.S. Ser. No. 10/853,585 to DeJovin et al.; U.S. Ser. No. 12/193,098 to Theobald et al., etc.

In the present invention, crystalline particles of methylparaben have been unexpectedly observed in some brimonidine topical gel formulations and placebo formulations containing carbomer and methylparaben.

There is a need for topical gel compositions containing carbomer and methylparaben that are substantially free of paraben crystalline particles and meet the antimicrobial requirement over an extended period of storage. Such compositions and related methods and products are described in the present application.

BRIEF SUMMARY OF THE INVENTION

In one general aspect, embodiments of the present invention relate to a topical gel composition comprising:
0.05 to 0.20% (w/w) methylparaben;
one or more second preservatives;
0.80 to 1.50% (w/w) carbomer; and
9.0 to 13.0% (w/w) total polyol;
wherein the topical gel composition has a pH of 4.5 to 7.5; and
wherein when the concentration of methylparaben is greater than 0.15% (w/w), the concentration of carbomer is less than 1.25% (w/w).

In another general aspect, embodiments of the present invention relate to a topical gel composition comprising:
0.01 to 5% (w/w) brimonidine;
0.05 to 0.20% (w/w) methylparaben;
one or more second preservatives;
0.80 to 1.50% (w/w) carbomer; and
9.0 to 13.0% (w/w) total polyol;
wherein the topical gel composition has a pH of 4.5 to 7.5; and
wherein when the concentration of methylparaben is greater than 0.15% (w/w), the concentration of carbomer is less than 1.25% (w/w).

Another general aspect of the present invention relates to a topical gel composition comprising:
0.1 to 0.6% (w/w) brimonidine tartrate;
0.05 to 0.15% (w/w) methylparaben;
one or more second preservatives selected from the group consisting of sodium benzoate, phenoxyethanol, benzyl alcohol, imidazolidinyl urea, and diazolidinyl urea;
0.80 to 1.50% (w/w) carbomer;
4.5 to 6.5% (w/w) propylene glycol;
4.5 to 6.5% (w/w) glycerol; and
purified water;
wherein the pH of the topical gel composition is adjusted to a pH of 5.0 to 6.5 by an adequate amount of sodium hydroxide aqueous solution.

In another general aspect, embodiments of the present invention relate to a method of treating or preventing a skin disorder in a subject. The method comprises topically administering to a skin area of the subject a topical gel composition according to an embodiment of the present invention, wherein the skin area is, or is prone to be, affected by the skin disorder.

Other aspects, features and advantages of the invention will be apparent from the following disclosure, including the detailed description of the invention and its preferred embodiments and the appended claims.

DETAILED DESCRIPTION OF THE INVENTION

Various publications, articles and patents are cited or described in the background and throughout the specification; each of these references is herein incorporated by reference in its entirety. Discussion of documents, acts, materials, devices, articles, or the like which have been included in the present specification is for the purpose of providing context for the present invention. Such discussion is not an admission that any or all of these matters form part of the prior art with respect to any inventions disclosed or claimed.

Unless defined otherwise, all technical and scientific terms used herein have the same meaning as commonly understood to one of ordinary skill in the art to which this invention pertains. Otherwise, certain terms used herein have the meanings as set forth in the specification. All patents, published patent applications and publications cited herein are incorporated by reference as if set forth fully herein. It must be noted that as used herein and in the appended claims, the singular forms "a," "an," and "the" include plural references unless the context clearly dictates otherwise.

As used herein, "erythema or a symptom associated therewith" is intended to encompass any type or classification of redness of skin caused by hyperemia or congestion of the capillaries in the lower layers of the skin, and any symptom associated therewith. The term "erythema or a symptom associated therewith" encompasses skin redness or rash resulting from any causes. For example, it can be caused by skin injury, surgery and other procedures on the skin, infection, inflammation, emotion, exercise, heat (erythema ab igne), cold, photosensitivity, radiation therapy, allergy, hot flush diseases, medications, etc. Examples of "erythema or a symptom associated therewith" include, but are not limited to, photosensitivity, erythema multiforme, and erythema nodusum, and their associated symptoms. Photosensitivity is caused by a reaction to sunlight, which often occurs when some factors, such as an infection or a medication, increase the sensitivity to ultraviolet radiation. However, photosensitivity can also occur without any increased sensitivity to ultraviolet radiation. Erythema multiforme is characterized by raised spots or other lesions on the skin, which are usually caused by a reaction to medications, infections, or illness. Most erythema multiforme is associated with herpes simplex or mycoplasma infections. Erythema nodosum is a form of erythema that is accompanied by tender lumps, usually on the legs below the knees, and may be caused by certain medications or diseases.

In one particular embodiment of the present invention, the term "erythema or a symptom associated therewith" includes erythema of rosacea, i.e., erythema or a symptom associated therewith in a patient with rosacea. Rosacea is an inflammatory skin disorder that generally affects the cheeks, nose, chin, and forehead of a patient. The major symptom of rosacea is erythema, i.e., the abnormal redness of the skin.

The term "erythema or a symptom associated therewith" encompasses different degrees or grades of erythema or a symptom associated therewith, from mild to severe.

In view of the present disclosure, a skin area that is affected by erythema or that is prone to be affected by erythema can be identified using any diagnostic signs or means known in the art, and can be treated by methods according to embodiments of the present invention.

As used herein, "telangiectasia or a symptom associated therewith" refers to a visible, permanent abnormal dilation of blood vessels, such as arterioles and venules. A visible blood vessel is a blood vessel visually discernable as a line to an observer without the aid of magnifying equipment (other than spectacles normally used by the observer). In various aspects, a telangiectatic blood vessel can have a diameter of at least about 0.5 mm. Telangiectasias can be associated with numerous conditions, syndromes, diseases, and disorders. For example, a facial telangiectasia can be associated with age, sun exposure, and alcohol use. Other diseases, disorders, conditions, and syndromes associated with telangiectasias include, in non-limiting example, scleroderma, hereditary hemorrhagic telangiectasia (Olser-Rendu syndrome), ataxia-telangiectasia, spider angioma, cutis marmorata telangiectasia congenita, Bloom syndrome, Klippel-Trenaunay-Weber syndrome, Sturge-Weber disease, xeroderma pigmentosa, nevus flammeus, generalized essential telangiectasias (GET), angioma serpiginosum, spider naevi, CREST syndrome, basal cell carcinoma, and unilateral nevoid telangiectasia.

In one particular embodiment of the present invention, the term "telangiectasia or a symptom associated therewith" includes telangiectasia associated with rosacea, i.e., telangiectasia or a symptom associated therewith in a patient with rosacea.

In another particular embodiment of the present invention, the term "telangiectasia or a symptom associated therewith" includes sun-induced/photodamage telangiectasia.

The term "telangiectasia or a symptom associated therewith" encompasses different degrees or grades of telangiectasia or symptoms associated therewith, from mild to severe.

In view of the present disclosure, a skin area that is affected by telangiectasia or that is prone to be affected by telangiectasia can be identified using any diagnostic signs or means known in the art, and can be treated by methods according to embodiments of the present invention.

As used herein, the term "brimonidine" refers to the compound (5-bromo-quinoxalin-6-yl)-(4,5-dihydro-1H-imidazol-2-yl)-amine having the structure of Formula (I):

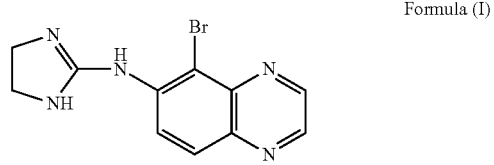

Formula (I)

and any pharmaceutically acceptable salt of the compound, such as brimonidine tartrate.

The phrase "pharmaceutically acceptable salt(s)," as used herein, means those salts of a compound of interest that are safe and effective for topical use in mammals and that possess the desired biological activity. Pharmaceutically acceptable salts include salts of acidic or basic groups present in the specified compounds. Pharmaceutically acceptable acid addition salts include, but are not limited to, hydrochloride, hydrobromide, hydroiodide, nitrate, sulfate, bisulfate, phosphate, acid phosphate, isonicotinate, acetate, lactate, salicylate, citrate, tartrate, pantothenate, bitartrate, ascorbate, succinate, maleate, gentisinate, fumarate, gluconate, glucuronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. Certain compounds used in the present invention can form pharmaceutically acceptable salts with various amino acids. Suitable base salts include, but are not limited to, aluminum, calcium, lithium, magnesium, potassium, sodium, zinc, and diethanolamine salts. For a review on pharmaceutically acceptable salts see Berge et al., 66 *J. Pharm. Sci.* 1-19 (1977), incorporated herein by reference.

As used herein, the term "hydrate" means a compound of interest, or a pharmaceutically acceptable salt thereof, that further includes a stoichiometric or non-stoichiometric amount of water bound to it by non-covalent intermolecular forces.

The term "topical gel composition" or "topical gel formulation," as used herein, means any gel formulation or composition which is pharmaceutically and/or cosmetically acceptable for topical delivery of the specified compound(s) according to embodiments of the invention.

As used herein, the term "composition" is intended to encompass a product comprising the specified ingredient in the specified amount, as well as any product which results, directly or indirectly, from combinations of the specified ingredient in the specified amount.

As used herein, the term "subject" means any animal, preferably a mammal, most preferably a human, to whom will be or has been administered compounds or topical formulations according to embodiments of the invention. The term "mammal" as used herein, encompasses any mammal.

Examples of mammals include, but are not limited to, cows, horses, sheep, pigs, cats, dogs, mice, rats, rabbits, guinea pigs, monkeys, humans, etc., more preferably a human. Preferably, a subject is in need of, or has been the object of observation or experiment of, treatment or prevention of a skin disorder, such as rosacea, erythema of rosacea, telangiectasia, psoriasis, purpura, erythema of acne, eczema, non-rosacea-related inflammation of the skin, flushing, skin sagging, creasing and/or wrinkling, or a symptom associated therewith.

In one embodiment, "treatment" or "treating" refers to an amelioration, prophylaxis, or reversal of a disease or disorder, or of at least one discernible symptom thereof. In another embodiment, "treatment" or "treating" refers to an amelioration, prophylaxis, or reversal of at least one measurable physical parameter related to the disease or disorder being treated, not necessarily discernible in or by the mammal. In yet another embodiment, "treatment" or "treating" refers to inhibiting or slowing the progression of a disease or disorder, either physically, e.g., stabilization of a discernible symptom, physiologically, e.g., stabilization of a physical parameter, or both. In yet another embodiment, "treatment" or "treating" refers to delaying the onset of a disease or disorder.

In certain embodiments, compounds of interest are administered as a preventative measure. As used herein, "prevention" or "preventing" refers to a reduction of the risk of acquiring a given disease or disorder. In a preferred mode of the embodiment, the specified compounds are administered as a preventative measure to a subject having a predisposition to a disease or disorder even though symptoms of the disease or disorder are absent or minimal.

In an embodiment of the present invention, methylparaben crystalline particles have been observed in brimonidine topical gel formulations containing 0.2% (w/w) or more methylparaben, particularly in batch sizes of 300 g to 250 kg. See Example 1 below. This observation is surprising in view of the solubility of methylparaben. According to a Material Safety Data Sheet (MSDS) of methylparaben, the solubility of methylparaben in water is about 0.25% (w/w) at 20° C. or about 0.30% (w/w) at 25° C. The solubility of methylparaben in propylene glycol is 1 in 5 at 25° C., the solubility of methylparaben in warm glycerol is about 1.4%, and see: MSDS, Chemicals & Laboratory Equipment, Science Lab.com, World Wide Web: sciencelab.com/msds.php?msdsId=9926083. Further, according to Handbook of Pharmaceutical Excipients (supra), the solubility of methylparaben in propylene glycol is 1 in 5 at 25° C., In view of methylparaben's solubility in polyols and water, it would have been reasonably expected that 0.30% (w/w) or less methylparaben would remain completely soluble in a topical gel composition comprising about 4.5 to 6.5% (w/w) of a first polyol in which methylparaben is substantially soluble, about 4.5 to 6.5% (w/w) of a second polyol, and about 90% (w/w) or less water. The detection of methylparaben crystalline particles in the composition is completely unexpected. Not wishing to be bound by theory, the methylparaben crystalline particles observed in the brimonidine topical gel and placebo compositions may have been caused by one or more reasons, such as recrystallization of methylparaben during the manufacturing process, or recrystallization of methylparaben during storage resulting from excipient-excipient interaction. Without the surprising observation made in the present invention, one would not have reasonably expected the existence of methylparaben crystals in the topical gel compositions, let alone to develop an improved topical gel formulation free of the crystals.

Embodiments of the present invention relate to an improved topical gel composition that is substantially free of crystalline particles and has microbiological quality over an extended period of storage. The improved topical gel composition according to an embodiment of the present invention comprises:

0.05 to 0.20% (w/w) methylparaben;
    one or more second preservatives;
    0.80 to 1.50% (w/w) carbomer; and
    9.0% to 13.0% (w/w) total polyol;
    wherein the topical gel composition has a pH of 4.5 to 7.5; and
    wherein when the concentration of methylparaben is greater than 0.15% (w/w), the concentration of carbomer is less than 1.25% (w/w).

According to embodiments of the present invention, the amount of methylparaben in the composition is about 0.05%, 0.075%, 0.10%, 0.125%, 0.15%, or 0.20% (w/w).

Suitable second preservatives that can be used in embodiments of the present invention include any preservatives that are suitable for topical application. Examples of the second preservatives include, but are not limited to, sodium benzoate, phenoxyethanol, benzyl alcohol, imidazolidinyl urea, or diazolidinyl urea. Additional examples of the second preservatives may include, quaternary ammonium compounds, such as benzalkonium chloride, benzethonium chloride, cetrimide, dequalinium chloride, and cetylpyridinium chloride; alcoholic agents, such as, chlorobutanol; antibacterial esters, such as esters of parahydroxybenzoic acid; and other anti-microbial agents such as chlorhexidine, chlorocresol, benzoic acid, polymyxin, mupirocin, erythromycin, clindamycin, gentamicin, polymyxin, bacitracin, silver sulfadiazine, etc.

Preferably, the second preservative is effective in inactivating challenge doses of Gram-negative and Gram-positive microorganisms, as well as yeast.

According to embodiments of the present invention, the one or more second preservatives comprise phenoxyethanol and the amount of phenoxyethanol in the composition is, or is greater than 0.3%, 0.35%, 0.4%, 0.45%, or 0.5% (w/w).

According to embodiments of the present invention, the carbomer is a synthetic polymer of acrylic acid cross-linked with polyalkenyl ethers or divinyl glycol. It can be a homopolymer of acrylic acid, cross-linked with an allyl ether pentaerythritol, allyl ether of sucrose, or allyl ether of propylene. Examples of carbomers that can be used in the present invention include, but are not limited to, carbomer 910, 934P, 940, 941, 1342, Carbopol® 974P (carbomer 974P), and Carbopol® 980 (carbomer 980).

Preferably, the carbomer is carbomer 934P, carbomer 974P, or carbomer 980.

According to embodiments of the present invention, the amount of the carbomer in the composition is about 0.8%, 0.85%, 0.95%, 1.05%, 1.15%, 1.25%, 1.35%, 1.45%, or 1.5% (w/w).

Polyol gel formulations with various ingredients solubilized therein have been used to minimize irritation when applied to the skin of a subject, while ensuring bioavailability of the active agent in the formulation. See Other III et al., "Gels and Jellies," pp. 1327-1344 of *Encyclopedia of Pharmaceutical Technology*, vol. 3 (ed. by Swarbrick et al., pub. by Marcel Dekker, Inc., 2002); or Pena, "Gel Dosage Forms: Theory, Formulation, and Processing," pp. 381-388 of *Topical Drug Delivery Formulations*, (ed. by Osborne et al., pub. by Marcel Dekker, Inc., 1990). Polyols in gel formulations can serve one or more functions, such as solubilizing agents, moisturizers, emollients, skin humectant, skin-penetration agents, etc. Suitable polyols that can be used in embodiments of the present invention include, but are not limited to, glycerine, propylene glycol, dipropylene glycol, hexylene glycol, butylene glycol, and liquid polyethylene glycols, such as polyethylene glycol 200 to 600, and glycerol.

According to embodiments of the present invention, the amount of the total polyols in the composition is about 9.0% to 13.0% (w/w), for example about 9.0%, 9.5%, 10.0%, 10.5%, 11.0%, 11.5%, 12.0%, 12.5%, or 13.0% (w/w).

In an embodiment of the present invention, the topical gel composition comprises at least a first polyol in which the methylparaben is substantially soluble.

Preferably, the topical gel composition comprises the first polyol and a second polyol, such as propylene glycol and glycerine, respectively.

According to embodiments of the present invention, the amount of each of the first and second polyols in the composition is independently about 4.5% to 6.5% (w/w), for example 4.5%, 5.0%, 5.5%, 6.0%, or 6.5% (w/w).

In a preferred embodiment, a topical gel composition according to embodiments of the invention further comprises a water dispersible form of titanium dioxide ($TiO_2$), preferably at an amount that is sufficient to mask the color of brimonidine or another colored ingredient in the formulation, but would not cause irritation to the skin. $TiO_2$ may cause mild irritation and reddening to the eyes, thus eye contact with the $TiO_2$-containing topically administrable composition should be avoided. Titanium dioxide imparts a whiteness to the topically administrable composition and helps to increase the opacity and reduce the transparency of the composition. Titanium dioxide absorbs, reflects, or scatters light (including ultraviolet radiation in light), which can help protect products from deterioration. Titanium dioxide can also be used as a sunscreen to protect the user from the harmful effects of ultraviolet radiation that is part of sunlight.

According to embodiments of the present invention, the amount of water dispersible form of titanium dioxide in the composition is about 0.04%, 0.0425%, 0.0525%, 0.0625%, 0.0725%, or 0.08% (w/w).

In another general aspect, a topical gel formulation according to an embodiment of the present invention further comprises an active pharmaceutical ingredient, such as an alpha adrenergic receptor agonist or a pharmaceutically acceptable salt thereof, that is effective to prevent or treat a skin disorder.

Alpha adrenergic receptor agonists are well known in the art. In a preferred embodiment, the alpha adrenergic receptor agonist may be an alpha-1 or alpha-2 adrenergic receptor agonist. The alpha adrenergic receptor agonists included in the invention may or may not show selectivity for either the alpha-1 or alpha-2 adrenergic receptors. For example, some may be considered as being both alpha-1 and alpha-2 adrenergic receptor agonists. More preferably, the alpha adrenergic receptor agonist may be a selective alpha-1 or a selective alpha-2 adrenergic receptor agonist.

Examples of selective alpha-1 adrenergic receptor agonists include oxymetazoline, phenylephrine, and methoxyamine. Examples of selective alpha-2 adrenergic receptor agonists include brimonidine, tetrahydrozoline, naphazoline, xylometazoline, epinephrine, and norepinephrine.

In an embodiment of the present invention, the active pharmaceutical ingredient comprises 0.01 to 5% (w/w) brimonidine. The active pharmaceutical ingredient can optionally include one or more pharmaceutically active ingredients in addition to brimonidine, including, but not limited to, medications used to treat the skin disorder or the underlying disease that causes the skin disorder, antihistamines to control itching, antibiotics, corticosteroids, intravenous immunoglobulins, acetaminophen, etc.

In a preferred embodiment, the brimonidine is brimonidine tartrate.

According to embodiments of the present invention, the amount of brimonidine in the topical gel composition is about 0.05% to 0.1%, 0.1% to 0.4%, 0.4% to 0.7%, 0.7% to 1%, 1% to 2%, 2% to 3%, 3% to 4%, or 4% to 5% (w/w). Preferably, the amount of brimonidine tartrate in the composition is about 0.1 to 0.6% (w/w).

In a preferred embodiment of the present invention, a topical gel composition comprises:
   0.1 to 0.6% (w/w) brimonidine tartrate;
   0.05 to 0.15% (w/w) methylparaben;
   one or more second preservatives selected from the group consisting of sodium benzoate, phenoxyethanol, benzyl alcohol, imidazolidinyl urea, and diazolidinyl urea;
   0.80 to 1.50% (w/w) carbomer;
   4.5 to 6.5% (w/w) propylene glycol;
   4.5 to 6.5% (w/w) glycerol; and
   purified water;
   wherein the pH of the topical gel composition is adjusted to 5.0 to 6.5 by an adequate amount of sodium hydroxide aqueous solution.

According to an embodiment of the present invention, the topical gel composition comprises greater than 0.3% (w/w) phenoxyethanol as the second preservative when 0.15% (w/w) or less methylparaben is used in the formulation.

A topical gel composition according to embodiments of the present invention can comprise additional pharmaceutically acceptable excipients, such as those listed in *Remington: The Science and Practice of Pharmacy,* 866-885 (Alfonso R. Gennaro ed., 19th ed., 1995); Ghosh, T. K. et al., *Transdermal and Topical Drug Delivery Systems* (1997), hereby incorporated herein by reference. Examples of the additional excipients include, but are not limited to, protectives, adsorbents, antioxidants, local anesthetics, buffering agents, surfactants, flavorants, fragrances, dyes, etc.

Suitable protective agents and/or cosmetic agents, and adsorbents can include, but are not limited to, dusting powders, zinc stearate, collodion, dimethicone, silicones, zinc carbonate, aloe vera gel and other aloe products, vitamin E oil, allantoin, petrolatum, titanium dioxide, and zinc oxide.

Suitable antioxidants can include, but are not limited to, ascorbic acid and its esters, sodium bisulfite, butylated hydroxytoluene, butylated hydroxyanisole, tocopherols, and chelating agents like EDTA and citric acid.

Suitable buffering agents can include, but are not limited to, acetate buffers, citrate buffers, phosphate buffers, lactic acid buffers, sodium buffer, and borate buffers.

A topical gel composition according to embodiments of the present invention can further include local anesthetics and analgesics, such as camphor, menthol, lidocaine, dibucaine, and pramoxine; antifungals, such as ciclopirox, chloroxylenol, triacetin, sulconazole, nystatin, undecylenic acid, tolnaftate, miconazole, clotrimazole, oxiconazole, griseofulvin, econazole, ketoconazole, and amphotericin B.

A topical gel composition according to embodiments of the present invention can further include one or more antiseptics, such as iodine, povidine-iodine, benzalkonium chloride, benzoic acid, nitrofurazine, benzoyl peroxide, hydrogen peroxide, hexachlorophene, phenol, resorcinol, and cetylpyridinium chloride.

The topical gel composition according to embodiments of the present invention can be prepared by mixing the ingredients of the composition according to known methods in the art, for example methods provided by standard reference texts such as: *Remington: The Science and Practice of Pharmacy,* 1577-1591, 1672-1673, 866-885 (Alfonso R. Gennaro ed., 19th ed., 1995); Ghosh, T. K. et al., *Transdermal And Topical*

*Drug Delivery Systems* (1997), both of which are hereby incorporated herein by reference.

The pH of the topical gel formulations of the invention are preferably within a physiologically acceptable pH range, e.g., within the range of about 4.5 to about 7.5, more preferably, of about 5.0 to about 6.5, such as a pH of about 5.1, 5.15, 5.2, 5.25, 5.3, 5.35, 5.4, 5.45, 5.5, 5.55, 5.6, 5.65, 5.7, 5.75, 5.8, 5.85, 5.9, 5.95, 6.1, 6.15, 6.2, 6.25, 6.3, 6.35, 6.4, 6.45, or 6.5. To stabilize the pH, preferably, an effective amount of a buffer is included. Acids or bases can be used to adjust the pH as needed.

In one general aspect, embodiments of the present invention relate to a method of treating or preventing a skin disorder, such as rosacea, erythema of rosacea, telangiectasia, psoriasis, purpura, erythema of acne, eczema, non-rosacea-related inflammation of the skin, flushing, skin sagging, creasing and/or wrinkling, or a symptom associated therewith, in a subject by topically administering to a skin area of the subject a topical gel composition according to an embodiment of the present invention, wherein the skin area is, or is prone to be, affected by the skin disorder. The relevant disclosures, e.g., on using brimonidine to treat the one or more of skin disorders, in U.S. Ser. No. 10/853,585 to DeJovin et al.; U.S. Ser. No. 10/626,037 to Scherer; U.S. Ser. No. 10/607,439 to Gil et al.; U.S. Ser. No. 10/763,807 to Shanler et al.; U.S. Ser. No. 12/193,098 to Theobald et al.; U.S. Patent Application Publication No. 2006/0264515 to DeJovin et al.; U.S. Ser. No. 12/621,942 to DeJovin et al.; U.S. Patent Application Publication No. 2005/0020600 to Scherer; and U.S. Patent Application Publication No. 2009/0130027 to Shanler et al., are herein incorporated by reference as if set forth fully herein.

In an embodiment of the present invention, the topically administrable composition comprises about 0.1% to 0.6% (w/w), such as about 0.1%, about 0.15%, about 0.18%, about 0.2%, about 0.25%, about 0.3%, about 0.35%, about 0.4%, about 0.45%, about 0.5%, about 0.55%, or about 0.6% by weight of brimonidine tartrate.

To treat or prevent a skin disorder, in view of the present disclosure, the topical gel compositions of the invention can be topically applied directly to the affected area in any conventional manner known in the art, e.g. by dropper, applicator stick, or cotton swab, as a mist via an aerosol applicator, via an intradermal or transdermal patch, or by simply spreading a formulation of the invention onto the affected area with fingers, a sponge, a pad, or wipes. Generally, the amount of a topical formulation of the invention applied to the affected skin area ranges from about 0.0001 g/cm² of skin surface area to about 0.05 g/cm², preferably 0.002 g/cm² to about 0.005 g/cm² of skin surface area. Typically, one to four applications per day are recommended during the term of treatment.

Methods of the present invention can be used in conjunction with one or more other treatments and medications for the skin disorder, such as the medications used to treat the underlying disease that causes the skin disorder, antihistamines to control itching, antibiotics, corticosteroids, intravenous immunoglobulins, acetaminophen, etc.

The other medicament or treatment can be administered to the subject simultaneously with, or in a sequence and within a time interval of, the administration of brimonidine, such that the active ingredients or agents can act together to treat or prevent the skin disorder. For example, the other medicament or treatment and brimonidine can be administered in the same or separate formulations at the same or different times.

Any suitable route of administration can be employed to deliver the additional treatment or medication including, but not limited to, oral, intraoral, rectal, parenteral, topical, epicutaneous, transdermal, subcutaneous, intramuscular, intranasal, sublingual, buccal, intradural, intraocular, intrarespiratory, or nasal inhalation.

This invention will be better understood by reference to the non-limiting examples that follow, but those skilled in the art will readily appreciate that the examples are only illustrative of the invention as described more fully in the claims which follow thereafter.

Example 1

Observation of Methylparaben Crystalline Particles in Topical Gel Compositions

Crystalline particles were first observed visually in a sampling of 7 tubes of a batch of brimonidine topical gel composition. These particles were isolated. The identity of the particles was analyzed by several analytical methods, such as HPLC test for identification by comparison of the retention time against standards, differential scanning calorimetry (DSC) for determination of melting point, NMR for a structural identification (by 1H and 13C), mass/mass with UV detector and QTOF to separate and identify the different masses, etc. Based on these analyses, it has been concluded that the observed crystals are crystals of methylparaben (hereinafter abbreviated as POBM or MPOB), which is a preservative used in the composition. According to the process used for manufacturing the batch, methylparaben was first dissolved in propylene glycol at 50° C. (122-140° F.) in the preservative phase.

Microscopic observations were performed on additional representative batches of brimonidine topical gel compositions and placebo gel compositions containing 1.25% (w/w) carbomer, POBM and other ingredients. The observations have been done on one tube of each batch, with the microscope Axiolab DRBKT Zeiss no. 023733.01 with a camera ICC Zeiss or the microscope Olympus BX60. The microscopic observations were done at 5° C. and room temperature.

As shown in Table 1, methylparaben crystalline particles were unpredictably observed in both brimonidine and placebo gel compositions containing 0.2% or 0.3% by weight methylparaben (POBM).

TABLE 1

Results of microscopic observations of representative batches of gel composition

| Date of Manufacturing | Composition | Microscopic Observation | Batch Size | No. Tubes Observed | Date of Observation |
|---|---|---|---|---|---|
| April 2008 | Placebo, 0.3% POBM | Crystals | 130 kg | 7 | Dec. 2008 |
| April 2008 | Placebo, 0.3% POBM | No crystal | 130 kg | 5 | Dec. 2008 |
| Jul. 1, 2009 | Placebo, 0.3% POBM | Crystals | 300 g-2 kg | 1 | Oct. 2009 |
| Aug. 25, 2009 | Placebo, 0.3% POBM 0.03% Brimonidine | Crystals | 300 g-2 kg 200-250 kg | 1 | Oct. 2009 |

TABLE 1-continued

Results of microscopic observations of representative batches of gel composition

| Date of Manufacturing | Composition | Microscopic Observation | Batch Size | No. Tubes Observed | Date of Observation |
|---|---|---|---|---|---|
| Sep. 2, 2009 | 0.3% POBM 0.06% Brimonidine | No crystal | 200-250 kg | 1 | Feb. 2010 |
| Sep. 7, 2009 | 0.3% POBM 0.07% Brimonidine | Crystals | 200-250 kg | 1 | Feb. 2010 |
| Jul. 6, 2009 | 0.3% POBM 0.18% Brimonidine | Crystals | 300 g-2 kg | 1 | Feb. 2010 |
| Sep. 15, 2009 | 0.3% POBM 0.5% Brimonidine | Crystals | 200-250 kg | 1 | Oct. 2009 |
| Jul. 16, 2009 | 0.3% POBM 1% Brimonidine 1% | Crystals | 200-250 kg | 1 | Feb. 2010 |
| Sep. 18, 2009 | 0.3% POBM 2% Brimonidine 2% | No crystal | 200-250 kg | 1 | Feb. 2010 |
| Sep. 29, 2009 | 0.3% POBM 0.06% Brimonidine | No crystal | 300 g-2 kg | 1 | Feb. 2010 |
| Sep. 10, 2009 | 0.3% POBM 1% Brimonidine | Crystals | 300 g-2 kg | 1 | Oct. 2009 |
| Sep. 17, 2009 | 0.3% POBM | No crystal | | 1 | Oct. 2009 |
| Jan. 12, 2010 | Placebo, 0.2% POBM 0.18% Brimonidine | Crystals | 300 g 800 g | 1 | Feb. 4, 2010 |
| Dec. 22, 2009 | 0.2% POBM | No crystal | | 1 | Feb. 10, 2010 |

Assays were conducted to estimate the concentration of methylparaben solubilized in a batch originally containing 0.3% (w/w) of methylparaben, in which crystalline particles were observed. Centrifugation was performed on the batch to collect crystals at the bottom of the centrifuge tube, thus removing them from the supernatant. The methylparaben concentration in the supernatant was measured and found to be about 0.2% (w/w), which was about 66% of the 0.3% (w/w) in the original formulation. The reduction in the concentration of soluble methylparaben in the composition raises non-conformity issues and may result in poor microbiological quality of the composition over an extended period of storage.

The presence of methylparaben crystalline particles in the topical gel formulations is surprising in view of the solubility of methylparaben. In order to find a solution to avoid the crystallization problem, several hypotheses have been postulated and evaluated to uncover the potential cause and possible solution of the problem.

Example 2

Improved Topical Gel Compositions Free of Methylparaben Crystalline Particles

Various changes to the formulation and the process of manufacturing the formulation have been made in order to obtain improved topical gel formulations that are free of the observed paraben crystals and have acceptable microbiological quality. For example, methylparaben, also named methyl parahydroxybenzoate (POBM), was replaced with the more water soluble Na POBM, but crystalline particles of Na POBM were still observed at 0.3% (w/w) Na POBM. Addition of 0.1% of EDTA into the formulation resulted in immediate recrystallization of the POBM at 0.3% (w/w) in the formulation, suggesting that the 0.3% (w/w) concentration of POBM may be too high.

Numerous formulations with different ingredients and varying concentrations of the ingredients were made and tested for the presence of the paraben crystals by microscopic observations. The microbiological quality of the formulations was also analyzed by using acceptance-test criteria in preservative-efficacy testing (PET) in the United States Pharmacopeia (USP) and the European Pharmacopoeia (EP).

Based on microscopic observations and PET analyses, it was found that improved topical gel compositions containing 0.05% to 0.20% (w/w) methylparaben; one or more second preservatives, such as 0.3% (w/w) or more phenoxyethanol; 0.80 to 1.50% (w/w) carbomer, such as Carbopol®974P NF; 9.0% to 13.0% (w/w) total polyol, such as 4.5 to 6.5% (w/w) of a first polyol, e.g., propylene glycol, 4.5 to 6.5% (w/w) of a second polyol, e.g., glycerol; and one or more other ingredients, such as purified water, titanium dioxide, optionally an effective amount of brimonidine tartrate, with a pH of 5.0 to 6.5 adjusted by an adequate amount of sodium hydroxide, were free of methylparaben crystals after an extended period of storage and passed criteria of EP and USP. See Table 2, in which the concentration of carbomer in each of the formulations was 1.25% (w/w).

TABLE 2

Results of microscopic observations and PET of topical gel formulations

| Batch Size (kg) | Preservative Concentration (w/w) | Period of Storage (weeks) | Microscopic Observation | PET Result |
|---|---|---|---|---|
| 2 | 0.1% MPOB 0.3% Phenoxyethanol | 21 | No crystal | Failed criteria A of EP at 48 hours |
| 200 | 0.1% MPOB 0.4% Phenoxyethanol | 24 | No crystal | Passed EP and USP |
| 2 | 0.125% MPOB 0.4% Phenoxyethanol | 12 | No crystal | Passed EP and USP |

TABLE 2-continued

Results of microscopic observations and PET of topical gel formulations

| Batch Size (kg) | Preservative Concentration (w/w) | Period of Storage (weeks) | Microscopic Observation | PET Result |
|---|---|---|---|---|
| 200 | 0.125% MPOB 0.4% Phenoxyethanol | 7 | No crystal | Passed EP and USP |

It was further discovered that when the amount of methylparaben was more than 0.15% (w/w), decreasing the amount of carbomer reduced the formation of methylparaben crystals. See, for example, Table 3.

TABLE 3

Results of microscopic observation of gel compositions

| Batch Size | Composition | Microscopic Observation |
|---|---|---|
| 300 G | POBM:0.2 Phenoxyethanol:0.3 Carbopol ® 980:1.25 | Crystals after one month storage at RT |
| 300 G | POBM:0.2 Phenoxyethanol:0.3 Carbopol ® 980:0.8 | No crystal observed after one month storage at RT |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A topical gel composition, comprising:
0.05 to 0.20% (w/w) methylparaben;
a second preservative;
0.80 to 1.50% (w/w) carbomer;
9.0 to 13.0% (w/w) total polyol; and
purified water;
wherein the topical gel composition has a pH of 4.5 to 7.5; and
wherein when the concentration of methylparaben is greater than 0.15% (w/w), the concentration of carbomer is less than 1.25% (w/w).

2. The topical gel composition of claim 1, comprising about 4.5% to 6.5% (w/w) of a first polyol.

3. The topical gel composition of claim 1, further comprising an alpha adrenergic receptor agonist.

4. The topical gel composition of claim 3, wherein the alpha adrenergic receptor agonist is an alpha-1 or alpha-2 adrenergic receptor agonist.

5. The topical gel composition of claim 4, wherein the alpha adrenergic receptor agonist is selected from the group consisting of oxymetazoline, phenylephrine, methoxyamine, tetrahydrozoline, naphazoline, xylometazoline, epinephrine, and norepinephrine.

6. The topical gel composition of claim 1, further comprising 0.04 to 0.08% (w/w) of a water dispersible form of titanium dioxide.

7. The topical gel composition of claim 1, wherein the carbomer is selected from the group consisting of carbomer 934P, carbomer 974P and carbomer 980.

8. The topical gel composition of claim 1, wherein the second preservative is selected from the group consisting of sodium benzoate, phenoxyethanol, benzyl alcohol, imidazolidinyl urea, and diazolidinyl urea.

9. A topical gel composition, comprising:
0.05 to 0.15% (w/w) methylparaben;
a second preservative selected from the group consisting of sodium benzoate, phenoxyethanol, benzyl alcohol, imidazolidinyl urea and diazolidinyl urea;
0.80 to 1.50% (w/w) carbomer;
4.5 to 6.5% (w/w) propylene glycol;
4.5 to 6.5% (w/w) glycerol; and
purified water;
wherein the pH of the topical gel composition is adjusted to 5.0 to 6.5 by an adequate amount of sodium hydroxide aqueous solution.

10. The topical gel composition of claim 9, wherein the second preservative is phenoxyethanol, present at an amount greater than 0.3% (w/w) of the total weight of the topical gel composition.

11. The topical gel composition of claim 9, further comprising 0.04 to 0.08% (w/w) of a water dispersible form of titanium dioxide.

12. The topical gel composition of claim 9, further comprising an alpha adrenergic receptor agonist.

13. The topical gel composition of claim 12, wherein the alpha adrenergic receptor agonist is an alpha-1 or alpha-2 adrenergic receptor agonist.

14. The topical gel composition of claim 13, wherein the alpha adrenergic receptor agonist is selected from the group consisting of oxymetazoline, phenylephrine, methoxyamine, tetrahydrozoline, naphazoline, xylometazoline, epinephrine, and norepinephrine.

15. A method of treating or preventing a skin disorder in a subject, comprising topically administering to a skin area of the subject the topical gel composition of claim 1, wherein the gel composition further comprises an alpha adrenergic receptor agonist selected from the group consisting of oxymetazoline, phenylephrine, methoxyamine, tetrahydrozoline, naphazoline, xylometazoline, epinephrine, and norepinephrine, and wherein the skin area is, or is prone to be, affected by the skin disorder.

16. The method of claim 15, wherein the skin disorder is rosacea, erythema of rosacea, telangiectasia, psoriasis, purpura, erythema of acne, eczema, non-rosacea-related inflammation of the skin, flushing, skin sagging, creasing and/or wrinkling, or a symptom associated therewith.

17. A method of treating or preventing a skin disorder in a subject, comprising topically administering to a skin area of the subject the topical gel composition of claim 9, wherein the gel composition further comprises an alpha adrenergic receptor agonist selected from the group consisting of oxymetazoline, phenylephrine, methoxyamine, tetrahydrozoline, naphazoline, xylometazoline, epinephrine, and norepinephrine, and wherein the skin area is, or is prone to be, affected by the skin disorder.

18. The method of claim 17, wherein the skin disorder is rosacea, erythema of rosacea, telangiectasia, psoriasis, purpura, erythema of acne, eczema, non-rosacea-related inflammation of the skin, flushing, skin sagging, creasing and/or wrinkling, or a symptom associated therewith.

* * * * *